United States Patent [19]

Davidson

[11] Patent Number: 5,549,667
[45] Date of Patent: Aug. 27, 1996

[54] MECHANICAL HEART WITH WEAR RESISTANT COATINGS OF REDUCED THROMBOGENICITY

[75] Inventor: James A. Davidson, Germantown, Tenn.

[73] Assignee: Smith & Nephew Richards, Inc., Memphis, Tenn.

[21] Appl. No.: 320,456

[22] Filed: Oct. 11, 1994

Related U.S. Application Data

[63] Continuation-in-part of Ser. No. 112,587, Aug. 26, 1993, Pat. No. 5,496,359, which is a continuation-in-part of Ser. No. 919,932, Jul. 27, 1992, Pat. No. 5,282,850, which is a continuation-in-part of Ser. No. 830,720, Feb. 4, 1992, Pat. No. 5,258,022, which is a continuation-in-part of Ser. No. 557,173, Jul. 23, 1990, Pat. No. 5,152,794, which is a continuation-in-part of Ser. No. 385,285, Jul. 25, 1989, Pat. No. 5,073,438.

[51] Int. Cl.$^6$ .................................................. A61M 1/10
[52] U.S. Cl. ............................................................. 623/3
[58] Field of Search ............................ 600/16, 17; 623/3

[56] References Cited

U.S. PATENT DOCUMENTS 3,685,059   8/1972   Bokros et al. ............................ 623/3
4,573,883   3/1986   Noon et al. ............................. 600/16

*Primary Examiner*—William E. Kamm
*Attorney, Agent, or Firm*—Pravel, Hewitt, Kimball & Krieger

[57] ABSTRACT

Hard, wear resistant, biocompatible and blood compatible coatings for components of external blood-contacting pumps including mechanical heart devices that are exposed to conditions of wear in the body and that may be exposed to blood components. The components may be fabricated from zirconium or the alloys of zirconium and the coatings comprise either blue-black or black zirconium oxide or zirconium nitride that are tightly adhered to the underlying metal substrate. In the event that the component is used under conditions which subject it to wear, then the coating should have a thickness that provides sufficient residual compressive stresses to withstand these conditions.

9 Claims, 3 Drawing Sheets

U.S. Patent   Aug. 27, 1996   Sheet 1 of 3   5,549,667 and a small transformer, worn by the patient, which trans-

5,549,667

MECHANICAL HEART WITH WEAR RESISTANT COATINGS OF REDUCED THROMBOGENICITY

STATEMENT OF RELATED APPLICATIONS

This application is a continuation-in-part of U.S. Ser. No. 08/112,587 filed Aug. 26, 1993, now U.S. Pat. No. 5,496,359, which is in turn a continuation-in-part of U.S. Ser. No. 07/919,932 filed Jul. 27, 1992 issued as U.S. Pat. No. 5,282,850; which is in turn a continuation-in-part of U.S. Ser. No. 830,720, filed Feb. 4, 1992, issued as U.S. Pat. No. 5,258,022 which is in turn a continuation-in-part of U.S. Ser. No. 557,173, filed Jul. 23, 1990, which is in turn a continuation-in-part of U.S. Ser. No. 385,285, filed Jul. 25, 1989, now issued as U.S. Pat. 5,073,438.

BACKGROUND OF THE INVENTION

1. Field of the Invention

This invention relates to hard, wear resistant, biocompatible and haemocompatible coatings on components of external blood-contacting pumps, including external mechanical heart devices, that may be exposed to conditions of wear in the body. The coatings reduce the rate of wear of components of the cardiac implant thereby increasing the life of the implant and, when applied to blood-contacting surfaces, the coatings present a blood compatible surface thereby reducing the risk of blood clotting.

2. Description of the Related Art.

Heart diseases, many of which cannot be cured by conventional surgery or drug therapy, continue to be a leading cause of death. For the seriously ill patient, heart replacement is often one of the few viable options available. While the National Heart, Blood and Lung Institute (NHBLI) estimates that up to 35,000 patients annually could benefit from heart transplants, only about 2,000 are performed each year, mainly due to a lack of availability of donor organs.

In 1988, the NHLBI began funding research and development for permanently implantable, electrically driven, total artificial hearts (TAHs). The pumping mechanism of the TAHs would be implanted into the chest cavity of the patient and the device would be powered by a battery pack and a small transformer, worn by the patient, which transmits energy to the heart with no physical connections through the skin. The NHBLI funded four separate groups: The Cleveland Clinic Foundation & Nimbus, Inc.; Pennsylvania State University & Sarns/3M; The Texas Heart Institute and Abiomed, Inc.; and the University of Utah. Consequently, four competing designs were developed.

The development of TAHs posed several issues. Firstly, it was necessary to duplicate the action of a human heart, ensure long-term reliability and biocompatibility, while producing a device that fits into the chest cavity in terms of both its total volume and the orientation of its connections to natural vessels in the body. Further, the design must fit a variety of patients, even though each patient is unique. In addition, a convenient and highly reliable power source for the heart must be developed.

Artificial hearts deliver approximately 8 liters of blood per minute at 110 mmHg pressure. It is desirable that the heart, in acting as a pump, should be as efficient as possible. A high level of efficiency means longer battery life and a longer period of operation between recharge intervals. Further, a highly efficient pump could also lead to the development of a smaller pump which facilitates implantation into the chest cavity.

Aside from the purely mechanical, wear, and power supply issues, it is also necessary that the design and materials prevent infection and thrombosis. Blood is a non-Newtonian fluid and its properties, such as viscosity, change with oxygen content, kidney function, and even the age of the patient. Further, plasma contains a suspension of fragile red blood cells which may be caught in artificial valves, or other mechanically stressful areas, thereby destroying these cells. It is therefore necessary to develop a pumping action that does not stress blood components material, and to fabricate the pump from materials that are not only biocompatible, but also "blood compatible" in the sense of minimizing damage to blood components and minimizing the formation of blood clots.

Many of the above comments also apply to ventricular assist devices (VADs), one of which is being developed by the Novacor Division of Baxter Health Care Corp. and which will apparently shortly undergo clinical trials. In the use of a VAD, the patient's heart remains in place while the VAD boosts the pumping pressure of the left ventricle of the heart. Consequently, the VAD is an assist device, rather than a replacement. However, the VAD must be blood compatible for the same reasons as the total artificial heart. Aside from the Novacor VAD, VADs have also been manufactured by Abiomed, Inc. and Thoratec, and Thermo Cardio Systems, Inc.

Several patents relating to TAHs and VADs have issued in recent years. These include U.S. Pat. Nos. 4,769,031; 4,750,903; 4,888,011; 4,902,291; 4,981,484; 4,994,078; and 5,066,300. While each of these patents describes an approach to the design of VADs, TAHs, or heart replacement devices like the Jarvik-7 for use outside the patient's body, none of them specifically address the materials to be used for those components which are subjected to mechanical wear, and microfretting wear, while being exposed to sensitive blood components and being subject to the corrosive effects of body fluids. Indeed, there exists a need for a material that is lightweight, biocompatible, and blood and tissue compatible with a hard surface that is resistant to abrasive wear, and microfretting wear, and the corrosive effects of body fluids, for use in heart assist or replacement devices (including EMHs, VADs and TAHs) to prolong the life of mechanical components while at the same time minimizing any deleterious effect on blood components.

SUMMARY OF THE INVENTION

The invention provides components for use in mechanical heart replacement or assist devices, such as external mechanical hearts (EMHs), total artificial hearts (TAHs) and ventricular assist devices (VADs), that are lightweight, strong and durable, that are biocompatible, while also being resistant to corrosive body fluids mechanical wear, abrasive wear, and microfretting wear. Further, the components have much improved blood compatibility in the sense of reduced risk of thrombogenesis (blood clotting).

More specifically, the invention provides both moving and nonmoving components that are fabricated from zirconium or zirconium alloys and that are coated with blue-black or black zirconium oxide, or with zirconium nitride. These coatings are produced on the surface of a zirconium or zirconium alloy component preferably by an in situ surface oxidation or nitridation so that the oxygen or nitrogen reacts at the surface of the metal thereby providing a tightly adherent coating. The in situ-formed coating forms a continuum with the underlying metal so that there is a less abrupt change in hardness between the metallic substrate and the coating, as may be found with other coating processes that involve the application of overlay coatings of various oxides, carbides, or nitrides onto metal substrates. While any thickness of coating above about 1 micron is useful in reducing blood clotting, the thickness of the hard surface layer or coating is desirably selected for the provision of sufficient residual compressive stresses to provide strength for counteracting the stresses that the component will encounter when in use. Moreover, the thickness of the surface coating is desirably such as to provide minimal dimensional change or distortion during the oxidation or nitridation process.

Due to the in situ method of formation of the zirconium oxide or nitrite coatings, a relatively uniform hard surface layer will form on all parts of the surface of the component, including inside diameters and corners. This provides a major advantage over "line of sight" type processes which may be used to apply pyrolytic carbon or other ceramic type overlay coatings, such as ion-assisted physical or chemical vapor deposition, or ion implantation.

Further, the use of zirconium or its alloys with their inherently low modulus (about 13 million psi) provide a more flexible lightweight construct for cardiovascular implant components. Thus, the low modulus improves contact stress levels where these might occur, and also improves the ability of certain TAH and VAD components to better accommodate blood flow to reduce thrombodynamic effects.

While zirconium metal itself may be used, its alloys are also useful and are preferred in many applications. These alloys include all those zirconium alloys, which when subjected to an oxidizing or nitriding atmosphere, will produce a tightly adherent hard oxide or nitride coating. It is understood that when a zirconium alloy is used, the oxide or nitride coating will also contain, to varying degrees, oxides or nitrides of the alloying constituents. In the specification and claims, such coatings are intended to fall within the definition of an in situ-formed zirconium oxide or zirconium nitride surface coating.

The oxide or nitride coatings may be further treated by silver doping or boronation to improve friction and wear characteristics or may be treated with selected agents known to further improve (reduce) reaction with blood, protein, and other body fluid constituents.

The invention blue-black or black zirconium oxide, or zirconium nitride coated components for artificial hearts including TAHs and VADs fabricated from zirconium or its alloys may be used wherever it is desirable to present a surface to the blood components that is blood compatible in the sense of reducing damage to blood components and reducing the potential for the formation of blood clots, and may also be used in those situations where it is desirable to enhance the life of the TAH or VAD by using a hard, wear and microfretting resistant surface.

DESCRIPTION OF THE PREFERRED EMBODIMENTS

The invention is of components for mechanical hearts, such as the external mechanical heart (EMH), the total artificial heart (TAH), and the ventricular assist device (VAD), that may be fabricated of zirconium or zirconium alloys and coated with a thin layer of blue-black or black zirconium oxide or zirconium nitride. This coating layer provides enhanced resistance to mechanical wear, microfretting wear, and corrosion by body fluids while also enhancing the blood compatibility of the invention components by reducing the risk of blood clot formation. Thus, the invention EMH, TAH, and VAD components not only extend the useful life of these devices but also significantly reduce the risks associated with adverse thrombogenic effects on the patient.

The invention coated components may be used for any of a range of applications, including but not limited to, those shown in the accompanying drawings and the components shown in U.S. Pat. Nos. 4,750,903; 4,769,031; 4,888,011; 4,902,291; 4,994,078; and 5,066,300, all of which are hereby incorporated by reference as if fully set forth. Similarly, the invention components may be substituted for those components of VADs subject to wear conditions and exposure to blood components.

The invention coated components also have the significant advantage that due to their hard surfaces, wear debris formation is negligible so that less foreign material is introduced into the body environment. Further, the ceramic-type coatings are tightly adherent and are highly resistant to spallation or separation from the underlying metal substrate, as may occur when the coating is only sprayed onto the metal surface or with hard overlay coating applied by techniques such as plasma vapor deposition or chemical vapor deposition.

Figure 1:
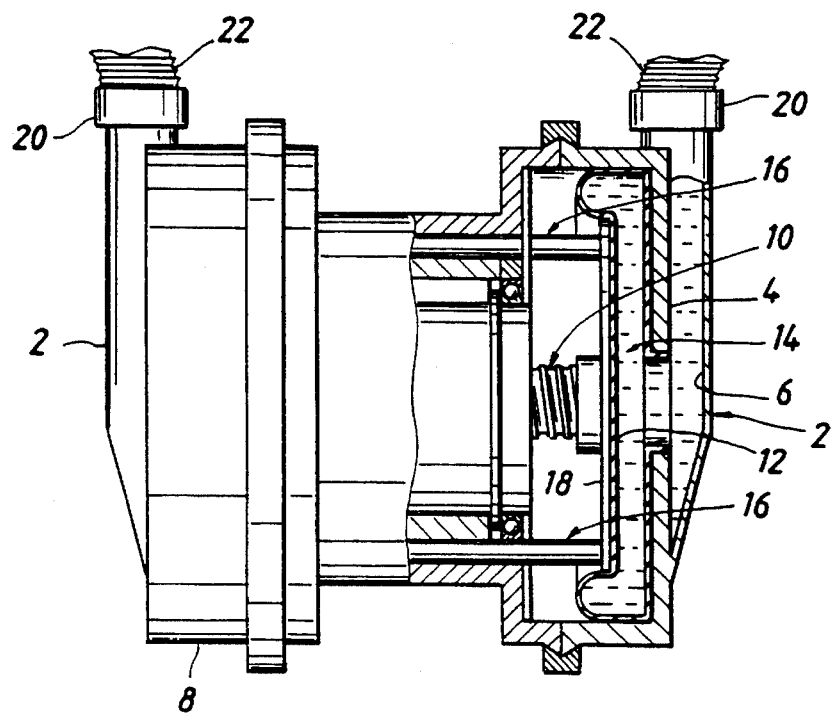
FIG. 1 is a schematic diagram of the Penn State/Sarns/3M design total artificial heart.

FIG. 1 is illustrative of the Penn State design which incorporates a stainless-steel roller screw 10 positioned between two flexible diaphragm blood pumps (right side pump 12 is shown, the other is within shell 8). A high speed, low torque brushless DC motor causes the roller screw 10 to turn thereby moving the roller screw shafts 16 linearly back and forth. To each end of the guide shaft 16 is attached a pusher plate 18. When the pusher plate 18 in the right side pump moves backward, blood is drawn into the pump space 14. At the same time, the pusher plate in the corresponding left side pump moves towards the left pushing blood out of its pump space. In this type of pump, the pusher plates 18 act against a flexible membrane 12, which is in contact with blood, and which can be inflated on the pump suction stroke and deflated on pump discharge stroke. The pusher plates are driven by the roller screw 10 and, thus, according to the invention, six revolutions of roller screw 10 are required for a full stroke with a motor speed of about 3,000 RPM. While planetary rollers are inserted between a roller screw nut and roller screw 10 to give rolling, not sliding contact and to spread mechanical load over many contact points, and while the entire roller screw system is hardened to minimize wear, the reliability of this system is improved by the use of the invention components. Thus, roller screw 10 and the roller-screw nut with which it is in rolling contact are both fabricated of zirconium or zirconium alloy and the surfaces are coated with either blue-black or black zirconium oxide or zirconium nitride. Further, the surfaces of the pump nozzles 2 shown as 4 and 6, connecting elements 20 and conduits 22, into and from which blood is continuously being pumped, may be fabricated from zirconium or zirconium alloy and coated on at least those surfaces presented to the blood components with zirconium nitride or blue-black or black zirconium oxide to minimize the potential for the formation of blood clots.

Figure 2:
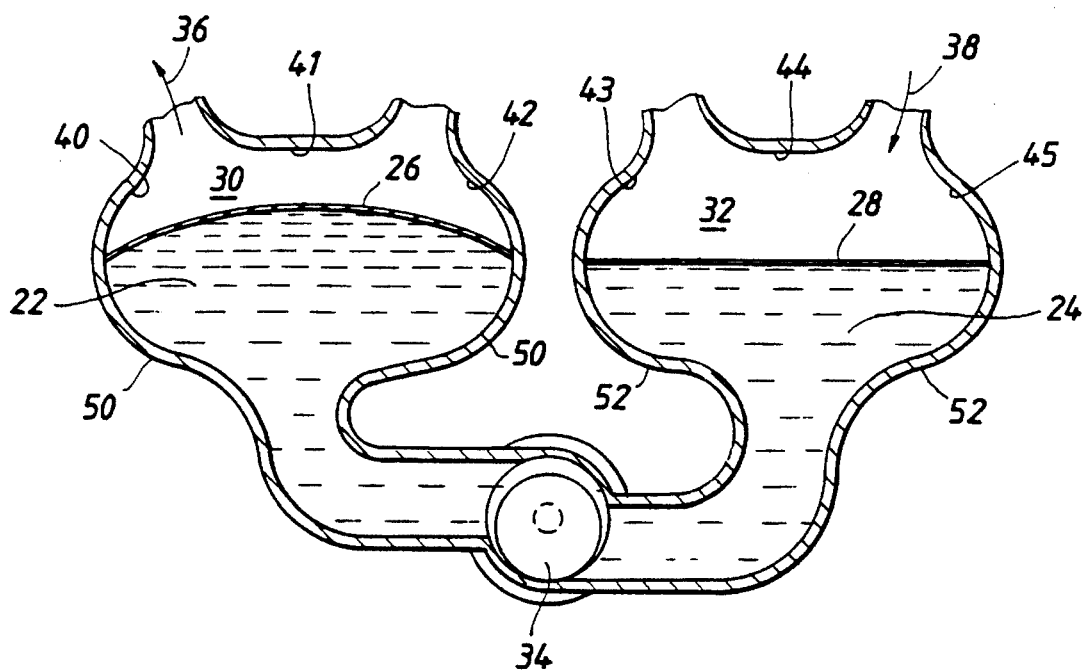
FIG. 2 is a schematic diagram of the University of Utah total artificial heart.

FIG. 2 is a schematic cross-sectional diagram of the University of Utah electrohydraulic heart. This heart includes shells 50 and 52 with a pump motor 34 interposed between them. In this type of heart, a motor 20 is used to pressurize silicon oil in regions 22 and 24 on the undersides of flexible diaphragms 26 and 28, respectively, to move blood in and out of the chambers 30 and 32 above the flexible diaphragms. For example, when motor 34 pressurizes silicon oil into chamber 22, then flexible diaphragm 26 expands upward and outwardly to push blood flow out of chamber 30 in direction 36. At the same time, silicon oil flows out of chamber 24 towards chamber 22 thereby allowing flexible diaphragm 28 to assume a natural position, shown in FIG. 2, and drawing blood into chamber 32 as shown from direction 38. Upon reversal of the direction of the bidirectional pump 34, the opposite effects are achieved.

Since the University of Utah pump is of a bidirectional design, and typically operates at speeds between 10,000–13,000 RPM in the high pressure direction and 5,000–8,000 RPM in the reverse, moving components of the pump are subject to microfretting and mechanical wear. Therefore, the invention components for the bidirectional axial flow pump 34 used in the University of Utah TAH design is fabricated from zirconium or zirconium alloy coated with a thin in situ formed layer of zirconium nitride or blue-black or black zirconium oxide, to reduce wear of the high speed components. Further, surfaces 40, 41, 42, 43, 44 and 45 are in direct contact with blood and should be coated with blue-black or black zirconium oxide or zirconium nitride to reduce the potential for blood clotting. Thus, the shells of the heart 50 and 52 may be fabricated of a zirconium alloy (or zirconium) to allow such coating.

Figure 3:
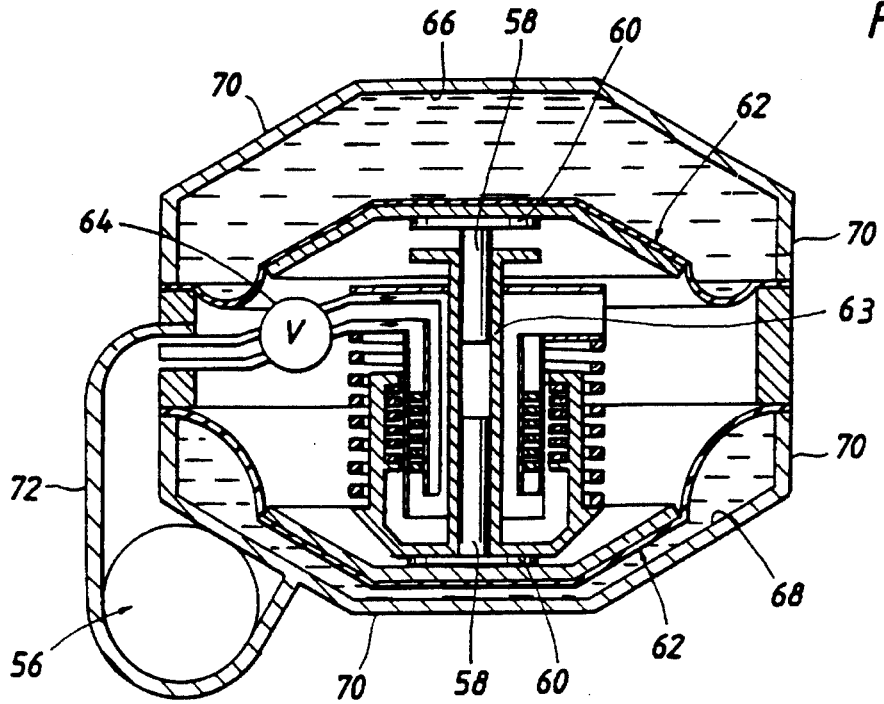
FIG. 3 is a schematic diagram of the Cleveland Clinic/Nimbus, Inc. total artificial heart.

FIG. 3 is a schematic cross-sectional illustration of the Cleveland Clinic TAH which utilizes a motor to turn a gear pump 56 which provides hydraulic pressure at about 100 psi to cause reciprocal movement of actuators 58 which in turn drive pusher-plates 60 that act on flexible diaphragms 62 to pump the blood. The actuators 58 operate slidingly within guide sleeve 63 so that wear on contact surfaces between actuator and sleeve may be expected. Further, the TAH has a flow reversing valve 64 with machine elements, such as bearing surfaces, subject to wear when the TAH is in use. Thus, TAH elements that are subject to wear and that may be advantageously fabricated of zirconium or its alloys and coated with blue-black or black zirconium oxide or zirconium nitride, include the guide sleeve 63, the actuators 58, the pump's gear elements and shaft and the rotary valve 64. Moreover, to reduce the risk of erosion damage to the pump from cavitation, the pump housing 72 may likewise be fabricated of the coated zirconium/zirconium alloys. Finally, internal surfaces 66, 68 of the heart housing 70 are in direct blood contact. Thus it is desirable to fabricate housing 70 from zirconium, or an alloy of zirconium, and coat at least the inner surfaces 66, 68 with blue-black or black zirconium oxide or zirconium nitride.

Figure 4A:
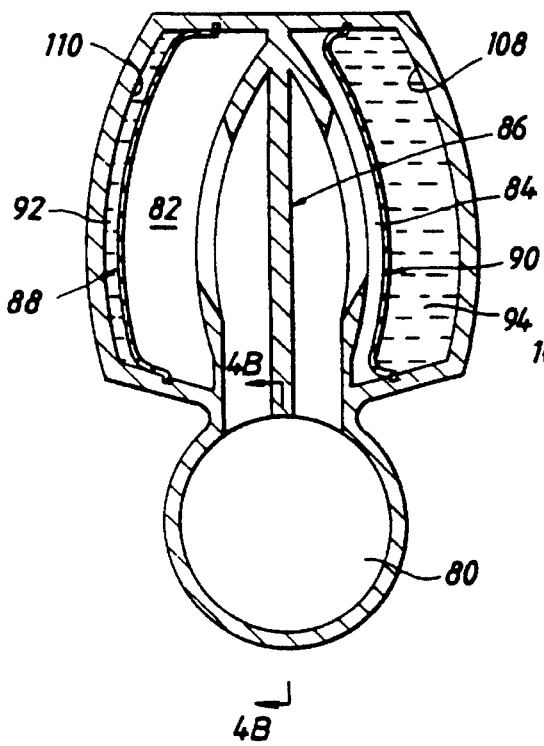
FIG. 4A is a schematic diagram in cross-section of the Texas Heart Institute/Abiomed total artificial heart.
Figure 4B:
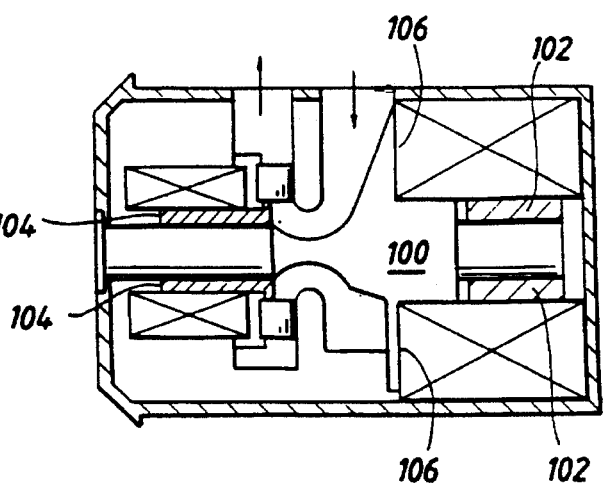
FIG. 4B is a side view in cross-section of the Texas Heart Institute/Abiomed total artificial heart of FIG. 4A.

FIG. 4 is a schematic diagram of the Texas Heart Institute/Abiomed TAH design which utilizes a d.c. motor to drive a miniature centrifugal pump 80 that rotates at about 6,000–8,000 RPM. This pump 80 pressurizes hydraulic fluid alternately into chambers 82 and 84 separated by septum 86 and enclosed by flexible diaphragms 88 and 90 respectively. As fluid is pumped into chamber 82, diaphragm 88 expands into heart space 92 forcing blood from this space. At the same time, fluid is pumped from chamber 84 causing diaphragm 90 to relax and expanding heart space 94, drawing blood into the TAH. The hydraulic flow is reversed by a two-position 4-way rotating valve 100 of radial configuration for compactness. Rotary valve 100 rotates within sleeves 102 and 104 at high speed so that contacting surfaces between the valve 100 and these sleeves are subject to wear. Further, rotary valve 100 rotates against seals 106 and wear may be expected at the contacting surfaces of the seals and the valve 100.

Several components of the Texas Heart Institute/Abiomed TAH may be fabricated according to the invention. Thus, high speed components of the centrifugal pump 80 subject to wear may be fabricated from zirconium or zirconium alloy and coated with blue-black or black zirconium oxide or zirconium nitride. Further, the rotary valve 100 itself and the surfaces of sleeves 102, 104 and seals 106 may be fabricated from zirconium or its alloys, coated with blue-black or black zirconium oxide or zirconium nitride to minimize wear. Finally, the inner surfaces of the TAH 108, 110 may be fabricated from zirconium or its alloys and coated with blue-black or black zirconium oxide or zirconium nitride to reduce the potential for blood clotting.

Figure 5A:
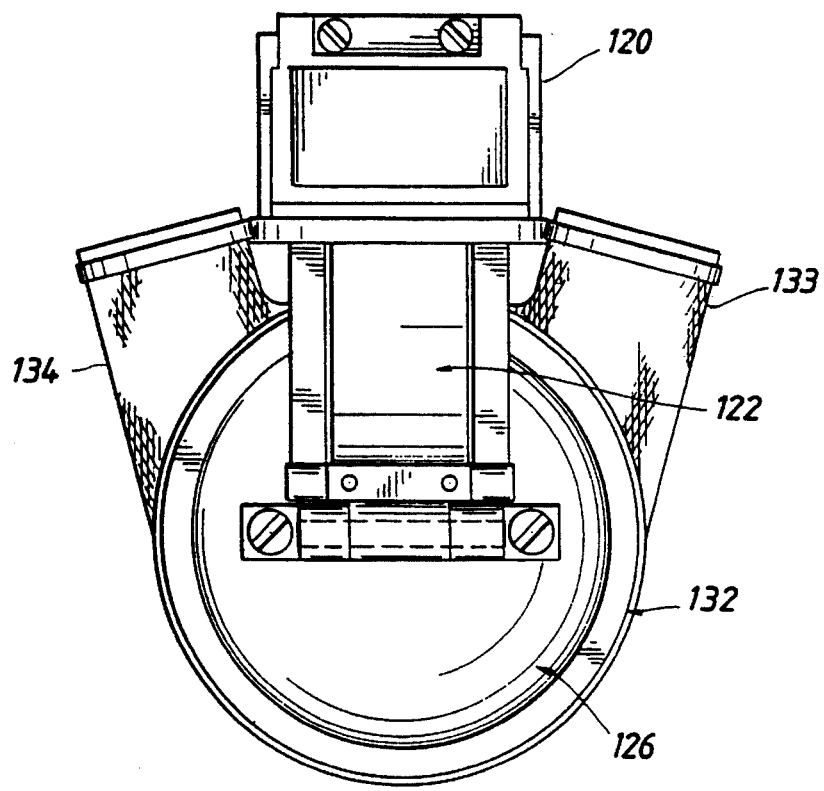
FIG. 5A and B are schematic diagrams of end and front views, respectively, of a ventricular assist device.
Figure 5B:
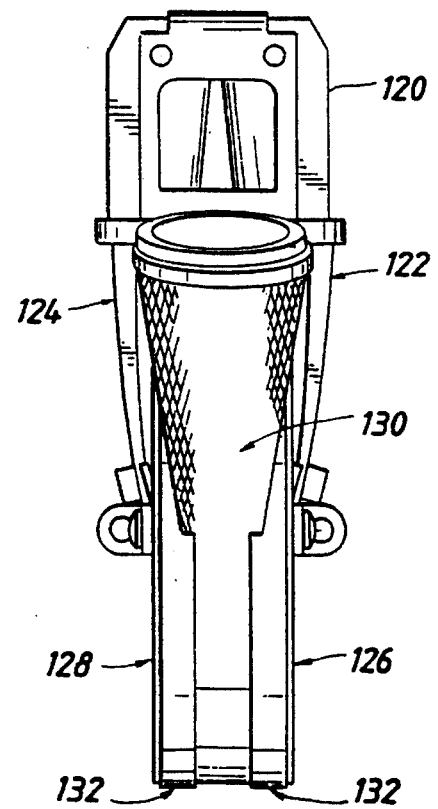

The Novacor designed VAD illustrated in FIGS. 5A and 5B has a solenoid mechanism 120 which sends energy through beam-springs 122, 124 that extend to the back of pump pusher plates 126, 128. The energy stored in the springs translates into linear motion of the plates which exerts force on the flexible blood sac 130. The blood sac 130 consists of a butyl rubber layer sandwiched between two layers of polyurethane Biomer. The blood sac 130 is supported within a cylindrical aluminum ring 132 that acts as a pump housing. The blood inflow 133 and outflow 134 ports are positioned tangentially on opposite sides of the housing to ensure straight-through blood flow. The ports are formed of an epoxy-impregnated Kevlar fabric shell that is integrated into the housing. The ports also encapsulate tri-leaflet inlet and outlet valves made from bovine pericardium tissue. When implanted into the body, fittings for attaching inflow and outflow valves to vascular conduits are bonded to a pump bulkhead, not shown, which also provides the framework for an encapsulating shell around the pump. This encapsulating shell also has provision for mounting the solenoid energy converter. The solenoid energy converter consists of two solenoid mechanisms, two lightweight titanium beam-springs, and an aluminum support structure. All of these metallic components would come into contact with blood components and body tissue. Therefore, the invention proposes that the titanium beam-springs be replaced with beam-springs of zirconium or zirconium alloy coated with blue-black or black zirconium oxide or zirconium nitride. Further, the aluminum support structure would likewise be replaced with a zirconium or zirconium alloy support structure coated with blue-black or black zirconium oxide or zirconium nitride. Novacor has identified, in designing the solenoid, that "the challenge was coming up with something that would run for 100 million cycles a year, without requiring maintenance." O'Connor, Lee, "Novacor's VAD: How to Mend a Broken Heart," Mechan. Engr'g pp. 53–55

(November 1991). The invention components fabricated from zirconium or zirconium alloys coated with blue-black or black zirconium oxide or zirconium nitride provides surfaces that are hard, fretting wear resistant, biocompatible and blood compatible so that they would meet this goal.

External mechanical hearts (EMHs) are used as a bridge to transplant. These hearts include the Jarvik-7 pneumatic heart and the more recent left-ventricular assist device, the Heartmate developed by Thermocardio Systems. In the Heartmate system, two tubes, one carrying air and the other electrical wire, pass from outside the body to an implanted blood pump. The pump is implanted in the abdomen and removes blood from the natural heart's left ventricle. This blood enters and exits the pump through 25 millimeter input and output valves made from chemically processed bovine tissue. The blood flows from the output valve through a dacron-wrapped polyurethane tube to the aorta. An electric motor mounted in the Heartmate's lower chamber actuates a flat-plate piston, which is bonded to a flexible polyurethane diaphragm. When the motor goes through one revolution, it turns a cam assembly that compresses the diaphragm, which pushes blood through the output valve. The operation of the pump is controlled by a microprocessor located in a shoulder bag which adjusts the heartbeat rate by changing the motor's current. According to the invention, the moving parts of the heartmate pump may be replaced with components fabricated from zirconium or its alloys, coated with blue-black or black zirconium oxide or zirconium nitride to reduce mechanical wear, friction and microfretting wear. Furthermore, those metallic components that come into contact with blood components, may also be replaced with zirconium or zirconium alloy components similarly coated to improve blood compatibility and reduce the risk of clot formation.

The gravest problem in the use of the pneumatic Jarvik-7 heart has been identified as the formation of blood clots. O'Connor, Lee, "Engineering a Replacement for the Human Heart," Mechan. Engr'g pp. 36–43 (July 1991). In 1990, the FDA withdrew the Jarvik system from clinical trials due to concerns over quality control during manufacture. The University of Utah made modifications to the design of the Jarvik heart to develop a new system called the "Utah 100" which has elliptical pump housings, as opposed to the spherical housings of the Jarvik-7. Further, the Utah 100 has redesigned junctions for joining the diaphragms within the ventricles to the housing. These changes are said to have resulted in an about 70% reduction in blood clot formation relative to the Jarvik-7 design. However, according to the invention, yet further reduction in blood clot formation may be obtained by fabricating moving parts and those metallic surfaces that contact blood components from zirconium or its alloys and coating these with a blue-black or black layer of zirconium oxide or zirconium nitride to increase blood compatibility, reduce wear and reduce microfretting wear.

In order to form continuous and useful zirconium oxide or nitride coatings over the desired surface of a metal alloy substrate, the metal alloy should contain from about 80 to about 100 wt. % zirconium, preferably from about 95 to about 100 wt. %. Niobium, tantalum, and titanium include common alloying elements in the alloy with often times the presence of hafnium. Yttrium may also be alloyed with the zirconium to enhance the formation of a tougher, yttria-stabilized zirconium oxide coating during the oxidation of the alloy, and relatively higher levels of oxygen will increase strength of the zirconium metal or alloy. While such zirconium and zirconium alloys may be custom formulated by conventional methods known in the art of metallurgy, a number of suitable alloys are commercially available. These commercial alloys include among others Zircadyne 705, Zircadyne 702, and Zircalloy.

The base zirconium containing metal alloys are cast or machined from wrought metal stock by conventional methods to the shape and size of component desired. The substrate is then subjected to process conditions which cause the natural (in situ) formation of a tightly adhered, diffusion-bonded coating of zirconium oxide on its surface. The process conditions include, for instance, air, steam, or water oxidation or oxidation in a fluidized or salt bath. These processes ideally provide a thin, hard, dense, blue-black or black, low-friction wear-resistant zirconium oxide film or coating of thicknesses typically less than several microns ($10^{-6}$ meters) on the surface of the component. Below this coating, diffused oxygen from the oxidation process increases the hardness and strength of the underlying substrate metal.

Unlike the prior art titanium oxides of, for example, Steinemenan's U.S. Pat. No. 3,643,658, the oxygen supplied to form the blue-black or black zirconium oxide coatings of the invention is a beneficial alloying component which improves the immediate substrate metal hardness which improves oxide attachment strength and durability and also improves the base-metal strength. Thus, the fatigue strength of the underlying zirconium metal is improved thereby increasing the potential life of the component. In contrast, oxygen in titanium alloys tends to stabilize the lower strength a-phase which significantly reduces the metal's fatigue strength.

The air, steam and water oxidation processes are described in now-expired U.S. Pat. No. 2,987,352 to Watson, the teachings of which are incorporated by reference as though fully set forth. The air oxidation process provides a firmly adherent black or blue-black layer of zirconium oxide ($ZrO_2$) of highly oriented monoclinic crystalline form. If the oxidation process is continued to excess, the coating will whiten and separate from the metal substrate. The oxidation step may be conducted in either air, steam or hot water. For convenience, the metal substrate may be placed in a furnace having an oxygen-containing atmosphere (such as air) and typically heated at 700–1100° F. up to about 6 hours. However, other combinations of temperature and time are possible. When higher temperatures are employed, the oxidation time should be reduced to avoid the formation of the white oxide.

While the blue-black or black zirconium oxide or nitride coatings have greatly increased blood compatibility in the sense of reduced risk of blood clot formation, and can be applied in thicknesses greater than about 1 micron, it is preferred that the coating range in thickness from about 1 to about 5 microns. For example, furnace air oxidation at 1000° F. for 3 hours will form an oxide coating on Zircadyne 705 about 3–4 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the component, will result. In general, thinner coatings (1–4 microns) have better attachment strength, and more favorable residual compressive surface stresses.

The thickness of the blue-black or black zirconium oxide coatings on the invention components provides a further distinction between the invention and the titanium oxide coatings of U.S. Pat. No. 3,643,658 to Steinemann. Titanium oxide films, whether prepared by high temperature (350° C.) oxidation or high current density anodizing, are thin, powdery and loosely adherent. This is because various forms of titanium oxide form as the oxide thickens. Consequently, these films can be more easily removed under fretting conditions in vivo exposing metal surface to body fluids with resulting metal ion release into the body tissue. The thicker, crystalline, more tightly adherent blue-black or black zirconium oxide films, by contrast, do not readily spall or separate from the alloy substrate and form essentially only one type of $ZrO_2$ oxide as compared to the multiple oxides for Ti and Ti alloys. It is speculated that the diffusion of oxygen into the underlying zirconium alloy provides a natural interlayer to which the zirconium oxide can adhere readily and tightly. Consequently, these zirconium oxide coatings provide excellent protection against abrasion and corrosion by body fluids.

One of the salt-bath methods that may be used to apply the zirconium oxide coatings to the metal alloy component, is the method of U.S. Pat. No. 4,671,824 to Haygarth, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°–800° C. (1022°–1470° C.). However, the lower oxygen levels in the bath produce thinner coatings than for furnace air oxidation at the same time and temperature. A salt bath treatment at 1290° F. for four hours produces an oxide coating thickness of roughly 7 microns. Residual contaminants in the salt bath may be inadvertently left on the treated implant surface and produce adverse clinical results. While some of these may be removed by polishing and washing, it is nonetheless preferred to use the gas (air) oxidation/nitridation processes which provides less possibility of contamination by other elements.

Whether air oxidation in a furnace, in a fluidized bed, or salt bath oxidation is used, the zirconium oxide coatings are quite similar in hardness. For example, if the surface of a wrought Zircadyne 705 (Zr, 2–3 wt. % Nb) component substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700–2000 Knoop hardness.

In situ air oxidation is the preferred method for producing the invention oxide coatings because it minimizes the potential for surface contamination, and allows oxygen diffusion into the metal substrate thereby allowing the formation of a tightly adherent oxide coating while also strengthening the zirconium metal.

While the above discussion has dealt mainly with blue-black or black zirconium oxide coatings on prostheses, zirconium nitride coatings are also effective in reducing wear on opposing surfaces and preventing corrosion of the underlying substrate by body fluids.

Even though air contains about four times as much nitrogen as oxygen, when zirconium or a zirconium alloy is heated in air as described above, the oxide coating is formed in preference to the nitride coating. This is because the thermodynamic equilibrium favors oxidation over nitridation under these conditions. Thus, to form a nitride coating the equilibrium must be forced into favoring the nitride reaction. This is readily achieved by elimination of oxygen and using a nitrogen or ammonia atmosphere instead of air or oxygen when a gaseous environment (analogous to "air oxidation") is used.

In order to form a zirconium nitride coating of about 5 microns in thickness, the zirconium or zirconium alloy component should be heated to about 800° C. for about one hour in a nitrogen atmosphere. Thus, apart from the removal of oxygen (or the appropriate reduction in oxygen partial pressure), or increasing the temperature, conditions for forming the zirconium nitride coating do not differ significantly from those needed to form the blue-black or black zirconium oxide coating. Any needed adjustment would be readily apparent to one of ordinary skill in the art.

When a salt bath method is used to produce a nitride coating, then the oxygen-donor salts should be replaced with nitrogen-donor salts, such as, for instance cyanide salts. Upon such substitution, a nitride coating may be obtained under similar conditions to those needed for obtaining an oxide coating. Such modifications as are necessary, may be readily determined by those of ordinary skill in the art.

Regardless of how the zirconium oxide or nitride surface layer is formed on the zirconium or zirconium alloy substrate, the friction and wear (tribological) aspects of the surface can be further improved by employing the use of silver doping or boronation techniques. Ion-beam-assisted deposition of silver films on zirconia ($ZrO_2$) ceramic surfaces can improve tribological behavior. The deposition of up to about 3 microns thick silver films can be performed at room temperature in a vacuum chamber equipped with an electron-beam hard silver evaporation source. A mixture of argon and oxygen gas is fed through the ion source to create an ion flux. One set of acceptable silver deposition parameters consists of an acceleration voltage of 1 kev with an ion current density of 25 microamps per $cm^2$. The silver film can be completely deposited by this ion bombardment or formed partially via bombardment while the remaining thickness is achieved by vacuum evaporation. Ion bombardment improves the attachment of the silver film to the zirconium oxide or nitride substrate. Similar deposition of silver films on the invention oxide or nitride coated TAH or VAD components may also be performed to improve tribological behavior.

An alternate method to further improve the tribological behavior of zirconium oxide or zirconium nitride coated surfaces is to apply boronation treatments to these surfaces such as commercially available boride vapor deposition, boron ion implantation or sputter deposition using standard ion implantation and evaporation methods, or form a boron-type coating spontaneously in air. Boric Acid ($H_3BO_3$) surface films provide a self-replenishing solid lubricant which can further reduce the friction and wear of the ceramic substrate. These films form from the reaction of the $B_2O_3$ surface (deposited by various conventional methods) on the ceramic (i.e., zirconium oxide) with water in the body to form lubricous boric acid. Conventional methods that can be used to deposit either a boron (B), $H_3BO_3$, or $B_2O_3$ surface layer on the surface include vacuum evaporation (with or without ion bombardment) or simple oven curing of a thin layer over the surface. The self-lubricating mechanism of $H_3BO_3$ is governed by its unique layered, triclinic crystal structure which allows sheets of atoms to easily slide over each other, thus minimizing substrate wear and friction.

A coating of phosphatidyl choline, commonly known as lecithin, may further be placed, as a final coating over those surfaces which are in contact with blood components, for the purpose of reducing thrombogenesis. Since the phosphatidyl choline layer does not have appreciable resistance to wear or microfretting, this coating is preferably only applied to those surfaces which are in contact with blood but not subject to significant gross wear or microfretting wear. While not wishing to be bound by any theory, it is speculated that the phosphatidyl choline layer operates by passivating the surface to which it is applied, thereby causing it to select against certain blood-borne matter binding to that surface. By this selective exclusion of certain blood components, such as albumin, from the blood surface, the likelihood of thrombogenesis is decreased. The phosphatidyl choline coating may be applied by any of the techniques known to persons of ordinary skill in the art, including immersing the component to be coated in a bath of phosphatidyl choline, or spraying or brushing the composition onto the surface.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

What is claimed is:

1. In an external mechanical heart of the type having a pump for receiving blood from a patient's heart and returning the blood to a patient's aorta, an input valve and an output valve, said pump and valves adapted and connected to remove blood from the heart and pump blood to the aorta, at least a portion of the external mechanical heart having surfaces that are subject to blood contact when in use, the improvement comprising:

at least a portion of the external mechanical heart being fabricated of a substrate metal selected from the group consisting of zirconium and alloys of zirconium, said substrate metal coated with a blood compatible coating formed by an in situ process, the coating being selected from the group consisting of blue-black zirconium oxide, black zirconium oxide and zirconium nitride, and the coating being tightly adherent to the substrate metal and covering the surfaces of the substrate metal that are subject to blood contact when the external mechanical heart is in use to reduce blood clot formation risk.

2. The improved external mechanical heart of claim 1, wherein the at least a portion of the external mechanical heart further includes a second coating selected from the group consisting of phosphatidyl choline, lubricous boron compositions and silver.

3. The improved external mechanical heart of claim 1, wherein the thickness of the blood compatible coating is from about 1 to about 5 microns.

4. In an external mechanical heart of the type having a pump for receiving blood from a patient's heart and returning the blood to the patients aorta, said pump including a piston, a cam assembly, an input valve and an output valve, the pump adapted and connected to remove blood from the heart and to pump blood to the aorta, at least a portion of the external mechanical heart being subject to conditions of wear, the improvement comprising:

at least a portion of the external mechanical heart being fabricated of a substrate metal selected from the group consisting of zirconium and alloys of zirconium, said substrate being subject to conditions of wear, and a hard, wear-resistant surface coating covering the substrate, said hard, wear-resistant surface coating selected from the group consisting of blue-black zirconium oxide, black zirconium oxide and zirconium nitride, and having a thickness in the range from about 1 micron to about 5 microns.

5. In an external mechanical heart of the type having a pump for receiving blood from a patient's heart and returning the blood to the patients aorta, an input valve and an output valve, said pump and valves adapted and connected to remove blood from the heart and pump blood to the aorta, the external mechanical heart having surfaces that are subject to blood contact when in use, the improvement comprising:

at least a portion of the external mechanical heart being fabricated of a substrate metal and a tightly-adherent, blood compatible coating over the surfaces of the substrate metal that are subject to blood contact when the external mechanical heart is in use, the coating selected from the group consisting of blue-black zirconium oxide, black zirconium oxide and zirconium nitride, the coating effective for reducing blood clot formation.

6. The improved external mechanical heart of claim 5, wherein the at least a portion of the external mechanical heart further includes a second coating selected from the group consisting of phosphatidyl choline, lubricous boron compositions and silver.

7. The improved external mechanical heart of claim 5, wherein the thickness of the blood compatible coating is from about 1 to about 5 microns.

8. In an external mechanical heart of the type having a pump for receiving blood from a patient's heart and returning the blood to the patients aorta, said pump including a piston, a cam assembly, an input valve and an output valve, the pump adapted and connected to remove blood from the heart and to pump blood to the aorta, at least a portion of the external mechanical heart being subject to conditions of wear, the improvement comprising:

a hard wear-resistant, tightly adherent coating of about 1 micron to about 5 microns thickness on at least a portion of the external mechanical heart that is subject to wear, said coating of a composition selected from the group consisting of blue-black zirconium oxide, black zirconium oxide and zirconium nitride.

9. The improved external mechanical heart of claim 8 wherein the at least a portion of the external mechanical heart is fabricated from a metal selected from the group consisting of zirconium and alloys of zirconium, and the hard wear-resistant, tightly adherent coating is formed by an in situ process.

* * * * *